United States Patent [19]

Lokken

[11] Patent Number: 5,758,660
[45] Date of Patent: Jun. 2, 1998

[54] STERILE ENVIRONMENT ENCLOSURE

[75] Inventor: Oddvin Lokken, Rye, N.Y.

[73] Assignee: Life Tech Systems Inc., Fairfax, Va.

[21] Appl. No.: 764,332

[22] Filed: Dec. 12, 1996

[51] Int. Cl.$^6$ ........................................ A61F 5/37
[52] U.S. Cl. .................. 128/877; 128/DIG. 26; 128/888; 604/164
[58] Field of Search ............ 128/845, DIG. 26, 128/846, 877, 878, 879, 888, 847; 600/21; 604/192, 198, 171

[56] References Cited

U.S. PATENT DOCUMENTS

| | | | |
|---|---|---|---|
| 3,850,172 | 11/1974 | Cazalis | 600/21 |
| 3,874,387 | 4/1975 | Barbieri | 128/888 |
| 3,881,477 | 5/1975 | Von Otto | 128/847 |
| 4,767,405 | 8/1988 | Lokken . | |
| 4,778,456 | 10/1988 | Lokken . | |
| 5,167,240 | 12/1992 | Rozier | 128/878 |

*Primary Examiner*—Michael A. Brown
*Attorney, Agent, or Firm*—Graham & James LLP

[57] ABSTRACT

An enclosure which provides a sterile environment for insertion of a catheter, attachment of an iv setup and the like and in another embodiment for sterile maintenance of a localized surgical site. The enclosure in both embodiments is comprised of a sterile transparent dome section comprised of a medically inert and acceptable resilient or rubber-like plastic material such as polyurethane, PVC or polyethylene, with a flat flange section peripherally situated around the base of the dome and extending away from the enclosure. The flange section comprises an adhesive section on the underface thereof whereby the dome can be sealingly and hermetically removably adhered to the skin of a patient to enclose a portion of a patient's skin in a controllable environment. The dome is provided with preformed apertures into which connection elements such as Luer lock fittings are inserted for sealed inlet connection to an oxygen source and an outlet, for infusion of sterilizing oxygen (the inlet being of smaller diameter to prevent pressure build-up) into the enclosed area and optionally for introduction of micropulverized bactericides for localized application. The dome, for catheter introduction further has an aperture for attachment of a cannula needle guide. For surgical applications, the enclosure itself is comprised of separable elements of base and dome which are press fit or otherwise hermetically engaged, with removal of the dome permitting access to the surgical site.

14 Claims, 4 Drawing Sheets

5,758,660

STERILE ENVIRONMENT ENCLOSURE

FIELD OF THE INVENTION

This invention relates to enclosures and shields which provide sterile environments for broken or ruptured skin areas and particularly for dermal puncture sites made for introduction of a catheter and skin cutting for minor surgical procedures.

BACKGROUND OF THE INVENTION

Broken, cut, or punctured skin, even in controlled environments, makes a patient very susceptible to dangerous infections. Thus, with dermal lesions such as bed sores, surgical lesions or cubitous ulcers, as well as during any procedure involving transdermal applications, such as introduction of a catheter in a skin puncture site, iv attachment, or surgery (even minor surgery) and the like, there is a real likelihood of infection of unprotected body parts from various sources including increasingly virulent air-carried sources, even in ostensibly "sterile environments". It has therefore been an objective in the past to locally control the atmosphere surrounding the opened skin site by heremetically enclosing it and irradiating the area with UV or constantly infusing the site with a bactericide such as pure oxygen or ozone or other sterilizing gas, or, in the case of surgery, prior to and immediately after exposure of a surgical site to ambient atmosphere.

In my prior U.S. Pat. No. 4,767,405, a sterile cassette, comprising a transparent raised sterile enclosure structure, is disclosed for such purpose. The cassette is comprised of a rigid, transparent (to permit to viewing of the enclosed skin for accurate placement of a needle or cannula) plastic in the form of a rectangular dome. The base of the cassette is described therein as comprising a flexible peripheral flange loaded with a skin adhesive (which is releasable for removal) for adhering the cassette to a patient's skin, surrounding a catheter insertion site via a skin puncture. The top of the cassette is a transparent, removable seal member which, when in place, maintains hermeticity within the skin-adhered dome. Transdermal infusions via a catheter are effected via introduction of a needle through a needle cannula guide which is integrally molded or formed in the walls of the dome and which remains in the skin after the needle is withdrawn. In addition, inlet and outlet fittings for oxygen or ozone circulation are also integrally molded or formed in the walls of the dome.

While effective and useful, the sterile cassette described in said patent entails high costs engendered by the need for co-molding or co-forming of the various parts of the dome and fittings. In addition, the rigid molded parts are restricted in movement and accordingly the manipulation of a needle cannula guide for effective placement is restricted thereby.

SUMMARY OF THE INVENTION

It is an object of the present invention to provide a low cost sterile enclosure for enclosing areas of broken skin such as sores or ulcers or for use with transdermal applications such as catheter placement; with separately sealingly connected, standard fittings including Luer locks; and to provide selective sealed placement of needle guide cannulas, with improvement in manipulation movement thereof.

It is a further object of the present invention to provide an openable sterile enclosure, as described, for use as a more sterile environment for surgical procedures (minor localized procedures or even major surgery) in place of a surgical drape.

It is a still further object of the present invention to provide a hermetically sealed environment with the localized atmospheric use of effective but small amounts of micropulverized antibiotic materials to the transdermal application site.

These and other objects, features and advantages of the present invention will become more evident from the following discussion and drawings in which:

SHORT DESCRIPTION OF THE DRAWINGS

DETAILED DESCRIPTION OF THE INVENTION

Figure 1:
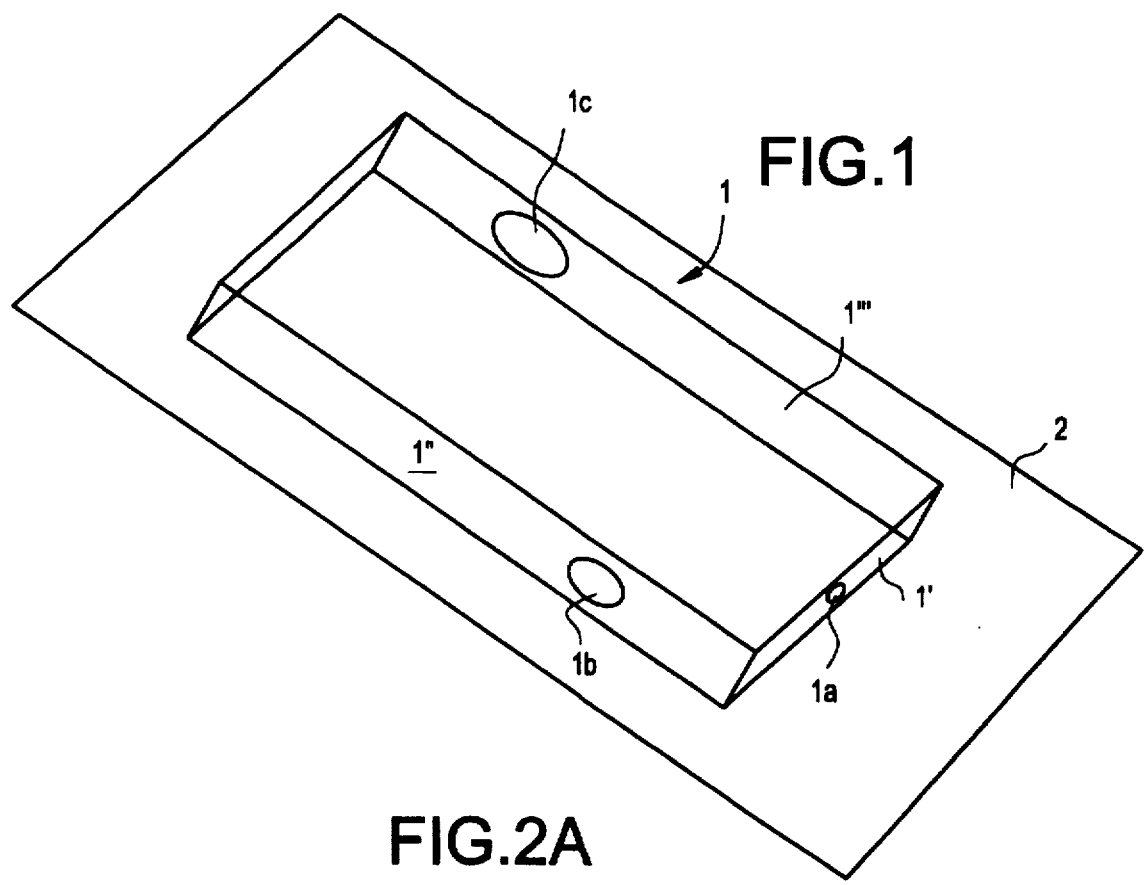
FIG. 1 is an isometric view of the enclosure of the present invention with apertures prior to placement of fittings therein.

Generally the present invention comprises a transparent enclosure member adapted to be sealingly adhered to the skin of a patient, to peripherally sealingly enclose an opened skin site, with the enclosure maintaining sterility of the enclosed site. The transparent enclosure is comprised of a medically inert flexible material capable of forming an elastomeric seal, wherein the enclosure comprises at least two apertures for sealed insertion of means for introduction and removal of a sterilizing gas and/or micropulverized antibiotics to the enclosed area. The transparent enclosure is sterile and is adapted to be sealingly adhered to the skin of a patient, to peripherally sealingly enclose a broken skin or transdermal application site (defined herein as a skin puncture site for catheter insertion and the like, or a skin cutting site for localized surgery), with the enclosure maintaining sterility of the enclosed site. The transparent enclosure is comprised of a medically acceptable inert flexible material, such as synthetic rubber, e.g., polyurethane; polyethylene, or polyvinyl chloride (PVC), etc., all of medical grades USP Class VI, which are capable of being both transparent and of forming an elastomeric seal. The enclosure is provided with means for permitting substantially non-pressurized infusion of oxygen or other sterilizing gas and/or sterilizing atmosphere (e.g., containing micropulverized antibiotic) to the enclosed area and the removal thereof (to prevent unwanted pressurization).

The enclosure is further provided with means to effect a transdermal application. In one embodiment these means comprise an externally manipulable needle cannula guide and in another embodiment the means comprise a removable section of the enclosure to permit direct access to the enclosed site, such as for local surgery.

In either embodiment, the enclosure is provided with multiple apertures. Each of the apertures is of a specified diameter and is adapted to receive a larger diameter member therein such as a gas fitting or sized elongated needle cannula guide. Because of the disparity of the diameters and the flexible nature of the enclosure material the enclosure material forms an air tight elastomeric seal around the inserted gas fitting or needle cannula guide.

To insure that the fitting or guide is not readily removed or dislodged during use, the fitting or guide is preferably provided with at least one circular flange. The flange is adapted to be of a size which can fit through an aperture, when stretched, and to abuttingly engage the inner wall surrounding the aperture in order to prevent accidental pull-out of the fitting. Alternatively, for more positive placement, two closely placed flanges are provided wherein a portion of the enclosure wall, peripheral to the aperture, is positioned between the adjacent flanges to prevent detrimental dislodgement movement (either into the enclosure or away from the enclosure). The fittings and guide are preferably provided with Luer lock engagements whereby external attachment to the fitting or guide is easily effected, in a sterile maintaining manner, with, for example, oxygen and pulverized antimicrobial sources or with an inserted needle cannula guide.

The enclosure may be initially fitted with the separable fittings and guides, such as by the manufacturer and supplied in a sterile package or it can be installed by the user and then sterilized prior to use. Alternatively, the fittings are positioned in the apertures of the enclosure, the enclosure is adheringly placed on the skin, and the enclosed area is sterilized with infusion of pure oxygen or other sterilizing gas, and/or UV irradiation, prior to the transdermal application.

The fittings in the enclosure are used to infuse the transdermal application site with pure oxygen, ozone and the like, and/or small amounts of micro-pulverized antibiotic materials. By using the enclosure to permit localized sterilization of the transdermal site, small amounts of the antibiotic may be applied directly to the possible site of infection. This obviates the need for relatively greater amounts of orally or intravenously introduced antibiotics, which, in such systemic amounts, generally have noxious side effects. It is preferred that the fittings, particularly the inlet fitting, further include microporous filtering means such as a microporous ceramic filter in order to control particle size and/or prevent introduction of particle contaminants.

The oxygen exhaust fitting is larger than the inlet fitting in order to prevent pressure build-up within the enclosure. The respective apertures for the fittings are appropriately sized for the elastomerically sealed engagement between the fittings and the respective apertures in the enclosure. It is preferred for a patient's comfort that the gas fittings be situated in the same side wall of the enclosure and that the side of the enclosure be closest to the free side of the patient where the enclosure is applied (i.e. left side of the enclosure for the left side of the patient and right side for the right side of the patient). As a result, the tubing does not irritatingly cross the patient's body except to the extent necessary to reach the enclosure from the nearest side.

Since the fittings and guide are not integrally molded with the enclosure, the enclosure can be more economically cast as a simple dome with formed apertures, and used with stock fittings and guides, adapted to particular requirements of the application. Thus, with multiple optional apertures for use with catheter insert into a patient's body, a needle cannula guide may be more accurately located. In addition, fittings and guides of varying lengths and configurations can be effectively utilized and interchanged, as required. Furthermore, the flexibility of the enclosure material lends itself for greater range in manipulating the cannula guide. For maximum effectiveness, the size of the cassette should be minimized, with dimensions of a typical enclosure for use in insertion of a catheter, being about 2 cm in height by 3.5 cm in width and about 10 cm in length (excluding flange dimensions). These dimensions, are of course, non limiting with, for example, applications for pediatric use being smaller and generally the size and body type of the patient determines an appropriate size for the enclosure.

In the embodiment adapted to be utilized in place of a surgical drape, the enclosure is comprised of two interfitting sections. The first is a base section having the adhering flange and the second section is a closed domed section adapted to be snap fit over the first to effect a sealed enclosure, with or without an adhesive connection between the sections. The fittings for gas infusion and introduction of antibiotics are placed through apertures in the second section. If desired, for more proximate flow of gas to the surgery site, the fittings may be made to extend through the base section. The size of this enclosure is dependent on the size of the surgical site and the available skin for effective adhesion.

DETAILED DESCRIPTION OF THE DRAWINGS AND THE PREFERRED EMBODIMENTS

Figure 1A:
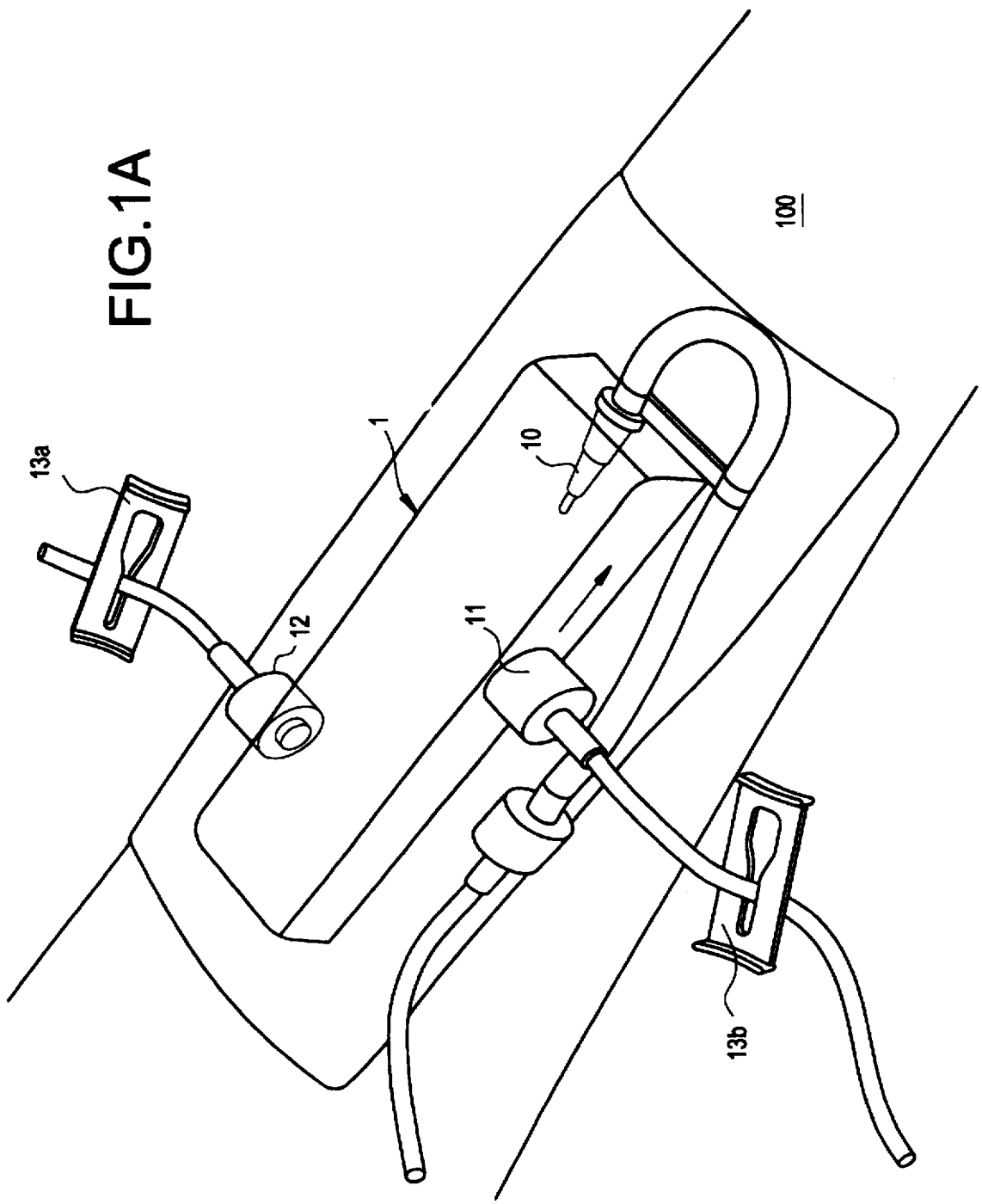
FIG. 1a depicts placement of the enclosure of FIG. 1 on a patient's arm, with Luer lock oxygen inlet and outlet fittings and connections and catheter placement, with needle insertion guide.

With specific reference to the drawings, in FIG. 1, surgical enclosure 1 is shown with adhesive flange 2 for placement on a patient's skin such as arm 100 in FIG. 1a. Enclosure 1, as shown, has three apertures integrally formed therein. Aperture 1a is situated on end wall 1' of the enclosure and is adapted for insertion of cannula needle guide 10 shown in FIG. 1a. Aperture 1b is for oxygen inlet fitting 11 and aperture 1c is for oxygen outlet fitting 12, shown in FIG. 1a (as described above, the inlet and outlet fittings are preferably on a single side when the enclosure is used at the side of the patient or simply to minimize a tangle of tubing from various directions).

Figure 2A:
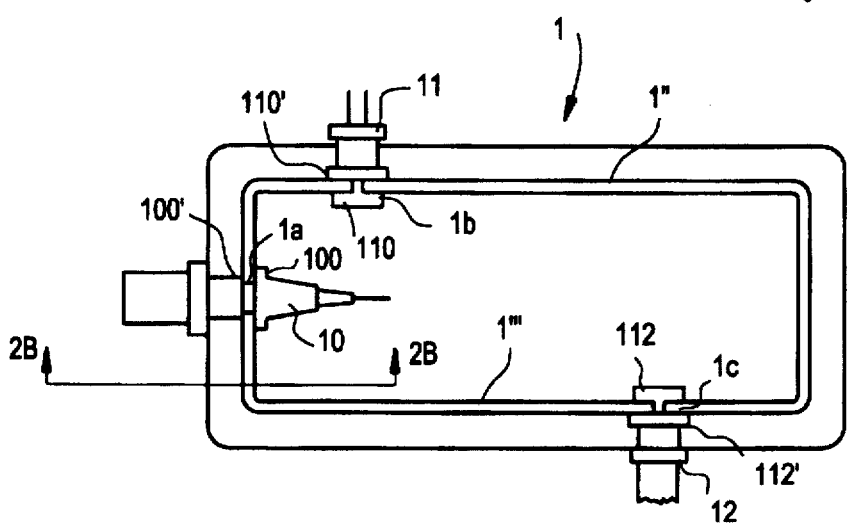
FIG. 2a is a top view through the transparent plastic material of the enclosure, showing Luer-like fittings for the puncturing needle and connections for oxygen infusion.

As seen more clearly in FIG. 2a, the oxygen outlet fitting 12 has a diameter of about twice that of oxygen inlet fitting 11 in order to insure that there is no pressure build-up in the hermetically sealed enclosure, to cause it to become forcibly detached from the patient's skin. Clamps 13a and 13b control the oxygen atmosphere in the enclosure 1, though exit clamp 13a should not be in a closed position if clamp 13b remains open, in order to also prevent pressure build-up.

As seen in FIG. 2a, fittings 11 and 12 and cannula needle guide 10 are snap fit within respective apertures 1a, 1b and 1c respectively and held therein by flange pairs 100–100', 110–110' and 112–112' respectively. Each of the guide 10 and fittings 11 and 12 are of Luer lock structure for rapid attachment and detachment as required.

Figure 2B:
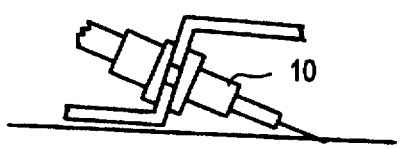
FIG. 2b is a side, partial section view taken along line 2b–2b of FIG. 2a, showing the needle orientation and placement.

The oxygen inlet and outlet fittings 11 and 12 are located in side walls 1" and 1'"respectively (though they could just as well be located on the same wall and often this is preferred). Cannula guide 10 is located in end wall 1' of the enclosure 1 for most expeditious manipulating positioning in finding an appropriate spot for needle insertion. As shown in FIG. 2b, end wall 1' deviates from the vertical to cause the cannula guide to be directed toward the skin surface. Similar tilting of side walls 1" and 1'" through which the oxygen fitting 11 and 12 extend, causes fitting 11 to direct oxygen directly on the puncture site and facilitates exhaust via fitting 12. In addition, the structure is more easily cast and used with a symmetrical configuration. For most applications, the enclosure 1 is provided with the three apertures shown. If desired, for greater flexibility, additional apertures may be provided as a choice for placement, with unused apertures being sealed. Because of the flexible nature of the material of which the enclosure is constructed (e.g., polyurethane), cannula guide 10 is fully movable for exact placement of the needle in an arc extending between enclosure walls 1' and 1'''.

Figure 3A:
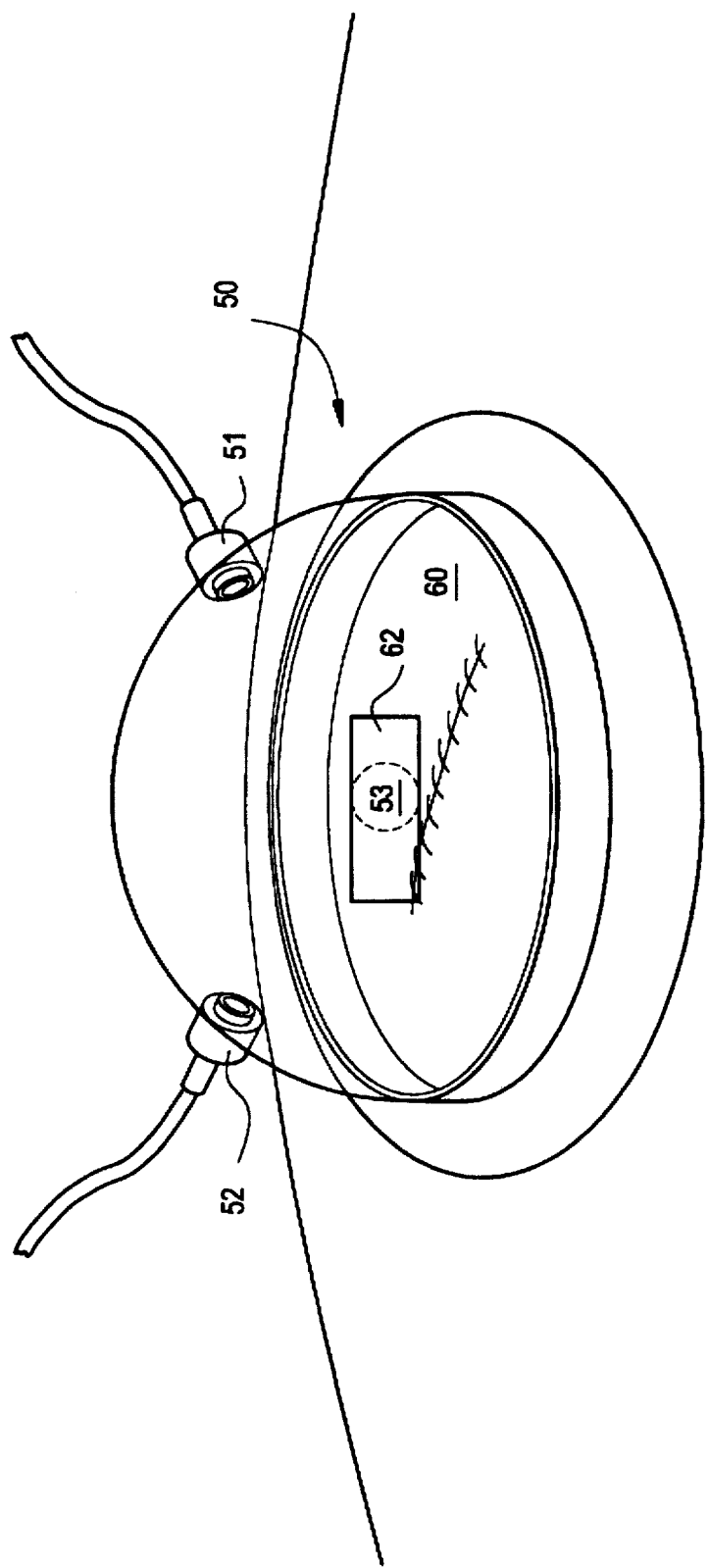
FIG. 3a is an isometric view of the enclosure of the present invention adapted for use as a localized surgical drape.
Figure 3B:
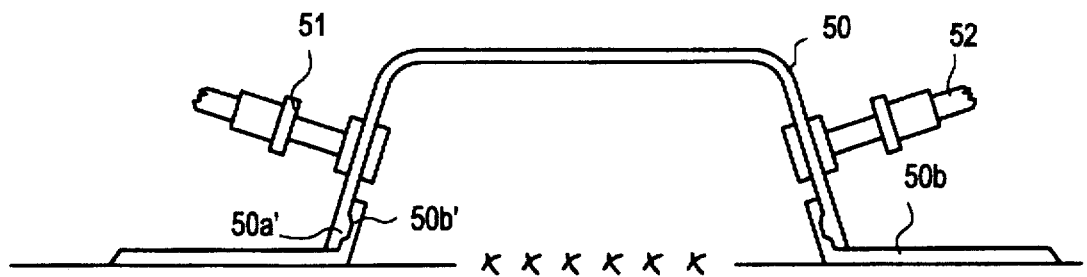
FIG. 3b is a side section view showing positioning of the oxygen fittings and the interlocking area between upper and lower sections.
Figure 4:
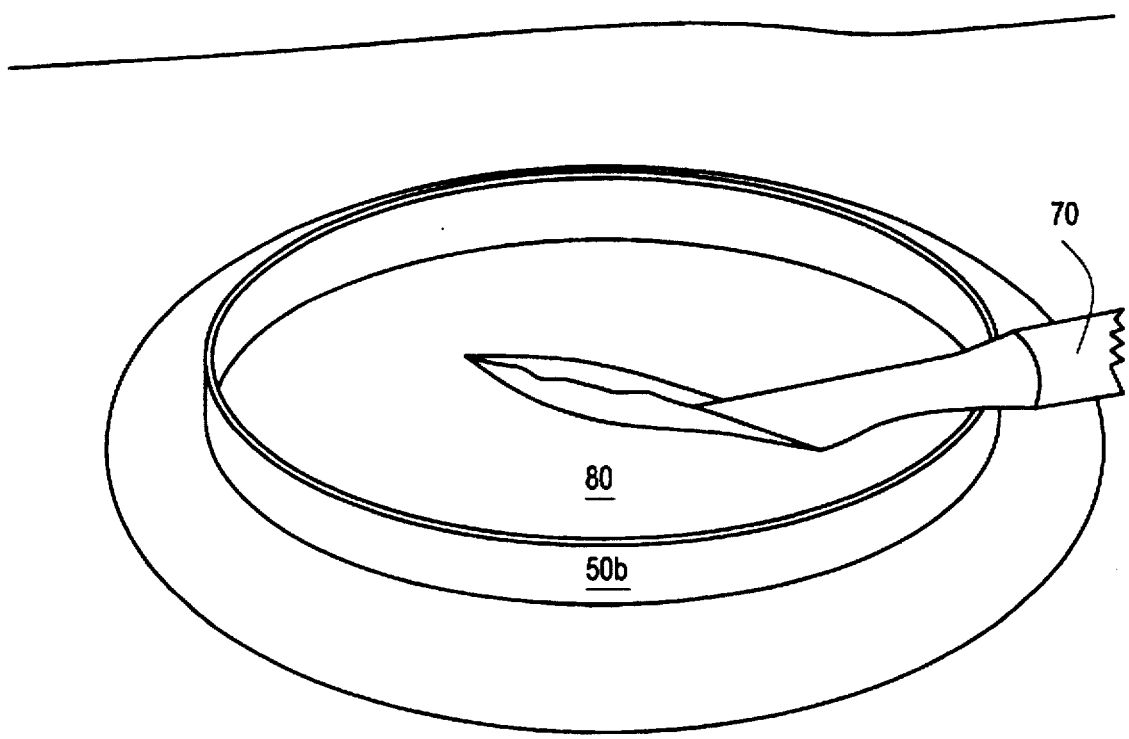
FIG. 4 is the enclosure of FIG. 3, with the top removed for localized surgical access.

In the embodiment shown in FIG. 3a, surgical enclosure 50 is shown in the configuration of a dome for isolating enclosure of incision area 60. Gas fittings 51 and 52 extend into the dome for infusion of sterilizing oxygen from fitting 51 and exhaust through fitting 52. Covered aperture 53 is available by peeling off of tape 62 for application of suction or introduction of medication. Micropulverized antibiotic materials can be introduced to maintain the incision free from infection by introduction with the oxygen or by application aperture 53, particularly after the surgical procedure has been completed and the site having been exposed as shown in FIG. 4.

Upper enclosure element 50a through which fittings 51 and 52 extend, comprises circular bead 50a' which is snap fit into corresponding groove 50b' of base element 50b to hermetically seal the enclosure. Adhesive is applied between the bead and groove when separation of the elements is no longer desired, such as after completion of the surgical procedure. As shown in FIG. 4, upper enclosure or dome element 50a, with the oxygen fitting is removed during surgery (shown with scalpel 70) with the enclosure base 50b functioning as a surgical drape around the incision. The surgical area 80 is then completely enclosed, isolated and sterilized with application of antibiotics and sterilizing oxygen.

It is understood that the above description and examples of preferred embodiments are only illustrative in nature and that changes in structure, materials and operative procedures are possible without departing from the scope of the present invention as defined in the following claims.

What is claimed is:

1. A transparent enclosure member adapted to be sealingly adhered to the skin of a patient, to peripherally sealingly enclose an opened skin site, with the enclosure maintaining sterility of the enclosed site, wherein the transparent enclosure is comprised of a medically inert flexible material capable of forming an elastomeric seal, wherein the enclosure comprises at least two apertures, with a first aperture for sealing insertion of means for introduction of a sterilizing gas to the enclosed area and a second aperture for removal of the sterilizing gas from the enclosed area.

2. The enclosure member of claim 1, wherein the means for removal of the sterilizing gas effectively removes the gas faster than the gas is being introduced whereby there is no significant pressure build up within the enclosure.

3. The enclosure member of claim 2, where the aperture for removal of a sterilizing gas is of sufficiently greater dimension than the aperture for introduction of the gas, whereby there is no significant pressure build up within the enclosure.

4. The enclosure member of claim 3, wherein the gas is one of oxygen or ozone, wherein the enclosure member contains a local atmosphere which consists essentially of oxygen or ozone.

5. The enclosure member of claim 3, wherein the enclosure member contains a local atmosphere having micropulverized antibiotic in amounts sufficient to treat the opened skin area against infection, with said micropulverized antibiotic having been introduced through one of the apertures.

6. The enclosure member of claim 2, wherein the enclosure member is further provided with means to permit effecting opening of the skin of the patient.

7. The enclosure member of claim 3, wherein the means to permit effecting opening of the skin of the patient comprises a third aperture and a cannula guide inserted therein and into an area enclosed by said enclosure member for insertion of a needle into the guide and into the enclosure and for perforation of the skin enclosed by the enclosure member.

8. The enclosure member of claim 3, wherein the means to permit effecting opening of the skin of the patient comprises said enclosure member comprising a removable element whereby the skin of the patient is externally accessible to effect opening of the skin and wherein the removable element comprises means for the sealing reclosing of the enclosure member.

9. The enclosure member of claim 8, wherein the means for introduction and removal of a sterilizing gas comprise respective fittings of larger diameter than that of respective apertures through which said respective fittings are inserted and elastically sealed within the respective apertures.

10. The enclosure member of claim 9, wherein the respective fittings comprise Luer lock configurations for attachment to external gas source and gas outlet means respectively and wherein each of said fittings each comprises means to prevent accidental removal thereof from the respective aperture.

11. The enclosure member of claim 7, wherein the means for introduction and removal of a sterilizing gas comprise respective fittings of larger diameter than that of respective apertures through which said respective fittings are inserted and elastically sealed within the respective apertures and wherein the cannula guide comprises a section adapted to be fitted within the third aperture and elastically sealed therein and wherein said cannula guide further comprises means to prevent accidental removal thereof from the aperture into which it is placed.

12. The enclosure member of claim 11, wherein the third aperture extends through a wall of the enclosure member, with said wall deviating from the vertical away from the skin of the patient such that said cannula guide, when inserted and positioned in said third aperture, extends toward the skin of the patient.

13. The enclosure member of claim 1, wherein the medically inert flexible material capable of forming an elastomeric seal, is comprised of medically acceptable grades of transparent material selected from the group consisting of polyurethane, polyethylene and polyvinyl chloride.

14. The enclosure member of claim 1, wherein the means for introduction and removal of a sterilizing gas to the enclosed area further comprises micro-filtering means.

* * * * *